United States Patent
Carrillo et al.

(10) Patent No.: US 8,298,178 B2
(45) Date of Patent: *Oct. 30, 2012

(54) RAPID EXCHANGE CATHETER WITH DEPRESSABLE CHANNEL

(75) Inventors: Oscar Carrillo, Attleboro, MA (US); James E. Windheuser, Hopkinson, MA (US); M. Kevin Richardson, Hopkinson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 257 days.

This patent is subject to a terminal disclaimer.

(21) Appl. No.: 12/254,425

(22) Filed: Oct. 20, 2008

(65) Prior Publication Data

US 2009/0099550 A1    Apr. 16, 2009

Related U.S. Application Data

(63) Continuation of application No. 11/366,739, filed on Mar. 2, 2006, now abandoned, and a continuation of application No. 10/298,313, filed on Nov. 15, 2002, now Pat. No. 7,037,293.

(51) Int. Cl.
  *A61M 37/00* (2006.01)
(52) U.S. Cl. .................................. 604/103.04
(58) Field of Classification Search ............. 604/103.04, 604/528
  See application file for complete search history.

(56) References Cited

U.S. PATENT DOCUMENTS

| | | | |
|---|---|---|---|
| 5,300,025 A | 4/1994 | Wantink | |
| 5,320,602 A | 6/1994 | Karpiel | |
| 5,324,269 A * | 6/1994 | Miraki | 604/160 |
| 5,389,087 A * | 2/1995 | Miraki | 604/247 |
| 5,397,302 A | 3/1995 | Weaver et al. | |
| 5,468,225 A | 11/1995 | Teirstein | |
| 6,007,522 A | 12/1999 | Agro et al. | |
| 6,312,374 B1 | 11/2001 | von Hoffmann | |
| 6,450,987 B1 * | 9/2002 | Kramer | 604/43 |
| 7,037,293 B2 * | 5/2006 | Carrillo et al. | 604/164.13 |
| 2002/0103472 A1 * | 8/2002 | Kramer | 604/507 |
| 2003/0100849 A1 | 5/2003 | Jang | |
| 2003/0163117 A1 * | 8/2003 | Ishii | 604/523 |
| 2009/0099550 A1 * | 4/2009 | Carrillo et al. | 604/528 |

FOREIGN PATENT DOCUMENTS

| | | |
|---|---|---|
| JP | 6-507805 | 9/1994 |
| JP | 2000-515305 | 11/2000 |
| WO | 92 / 20397 | 11/1992 |
| WO | 98 / 04011 | 1/1998 |
| WO | 01/66178 | 9/2001 |

* cited by examiner

*Primary Examiner* — Nicholas Lucchesi
*Assistant Examiner* — Diva K Chander
(74) *Attorney, Agent, or Firm* — Seager, Tufte & Wickhem, LLC

(57) ABSTRACT

A rapid exchange catheter extends from a proximal portion which remains outside of a patient's body during use to a distal portion which, during use, is located within a body lumen adjacent to a target area to be treated, wherein the proximal and distal portions are coupled by a medial portion. The catheter comprises a guide wire lumen extending longitudinally through the distal portion and a guide wire receiving channel formed by an outer surface of the medial portion, wherein the guide wire lumen is open to a distal end of the channel.

19 Claims, 4 Drawing Sheets

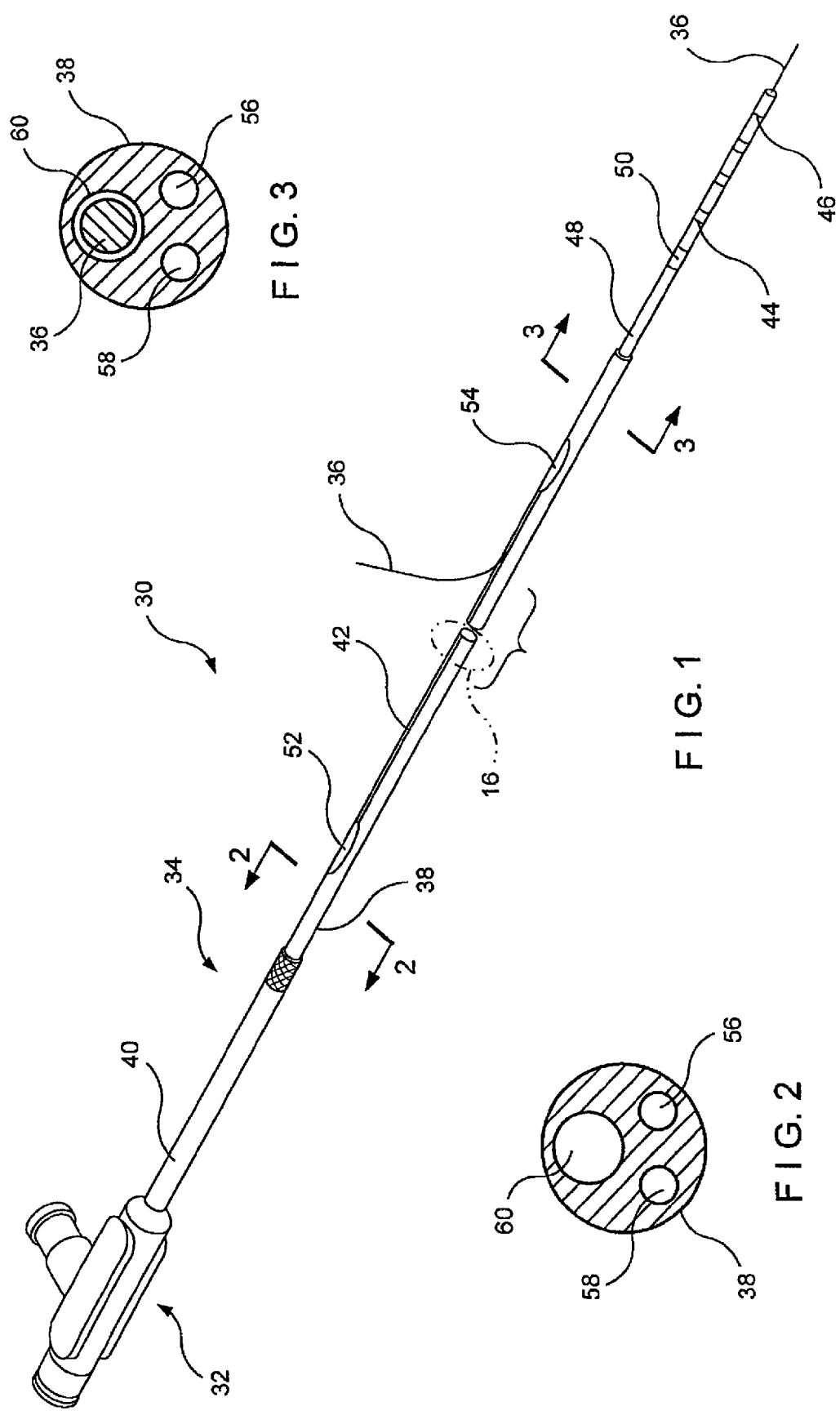

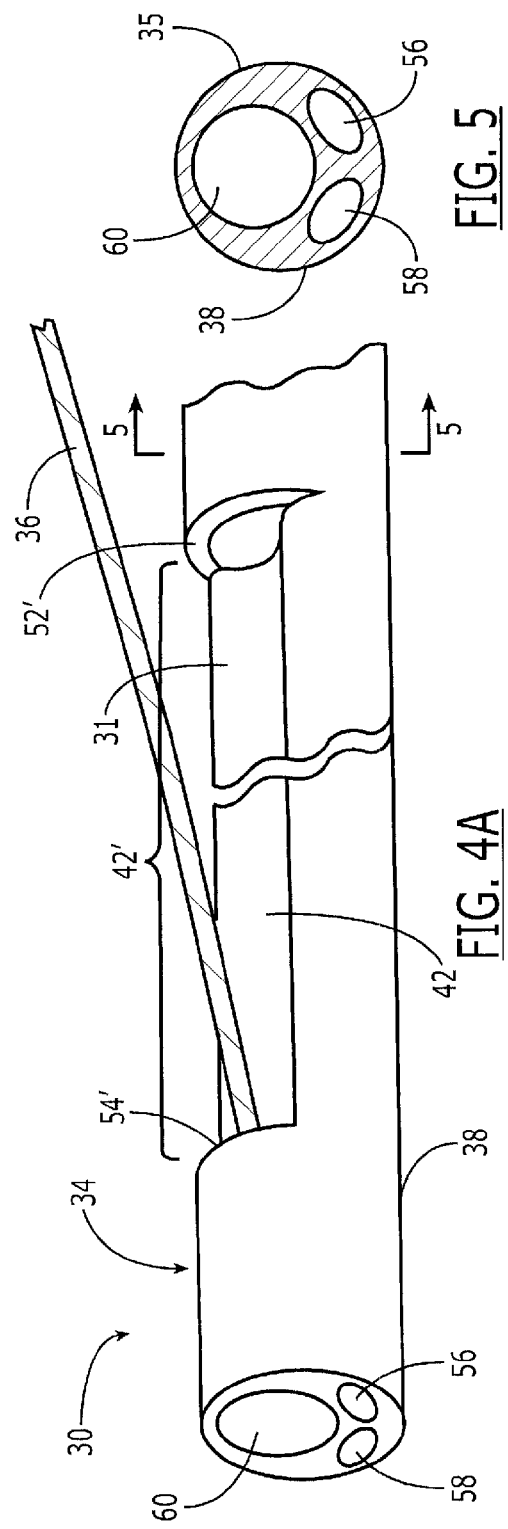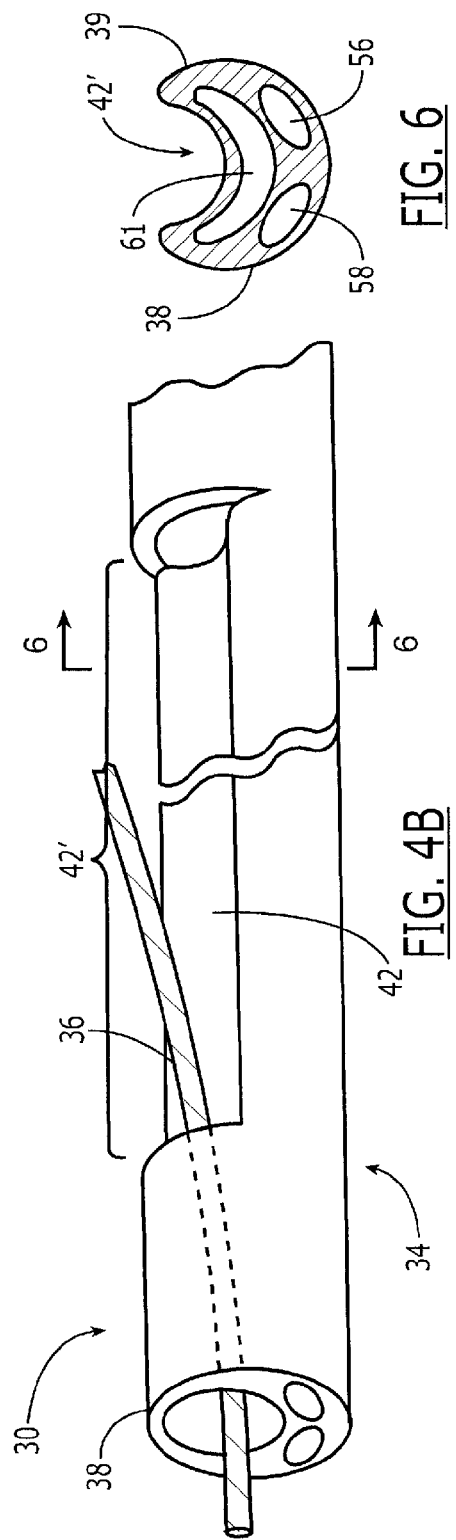

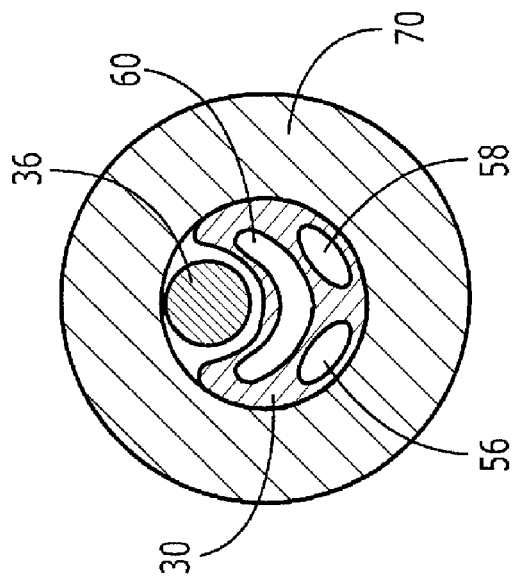
FIG. 8
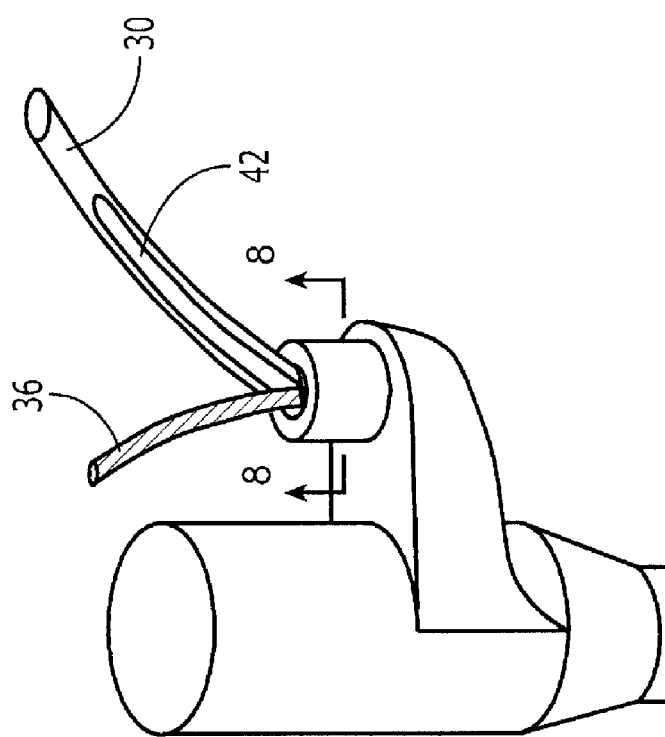
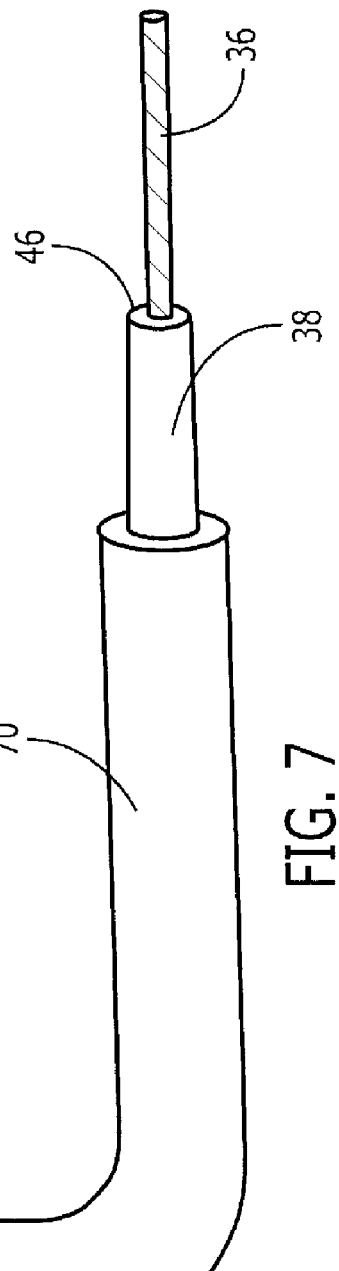
FIG. 7

RAPID EXCHANGE CATHETER WITH DEPRESSABLE CHANNEL

PRIORITY CLAIM

The present application is a Continuation application of U.S. patent application Ser. No. 11/366,739 filed Mar. 2, 2006 now abandoned entitled "Rapid Exchange Catheter with Depressible Channel" and U.S. patent application Ser. No. 10/298,313 filed Nov. 15, 2002 now U.S. Pat. No. 7,037,293 issued on May 2, 2006 entitled "Rapid Exchange Catheter with Depressible Channel", the entire disclosure of these applications which is expressly incorporated herein by reference.

FIELD OF THE INVENTION

The present invention relates generally to endoscopic procedures such as biliary procedures. More particularly, the present invention relates to rapid exchange catheters for such procedures.

BACKGROUND INFORMATION

Endoscopic procedures for treating pathologies within the alimentary canal and biliary tree, including the biliary, hepatic, and pancreatic ducts, are increasing in number. While an endoscope provides access to the general area of a desired duct using direct visualization, the duct itself must often be navigated using a catheter in conjunction with fluoroscopy and guide wires without steering assistance from the endoscope.

Multi-lumen catheters are known for a variety of endoscopic procedures including, for example, retrograde cholangiopancreatography, retrograde sphincterotomy and other therapeutic and diagnostic procedures. Furthermore, these endoscopic procedures have been performed using guide wire techniques. The present devices utilized in these procedures are often at least 180 cm long to allow them to pass through an endoscope, which is commonly at least 150 cm long. Therefore, when using such a catheter having a guide wire lumen extending the full length thereof, to allow for catheter and guide wire exchange while maintaining position within the target area, the guide wires used are often 400 cm long or longer. The exchange of devices over guide wires of this length is both time consuming and cumbersome.

Due to the length of the guide wire, physicians often require at least two assistants in the room to perform such procedures. Typically, one assistant is responsible for the patient and the device related concerns, while the other assistant is responsible for the guide wire. The additional hands required due to the length of the guide wire results in a procedure that is more time consuming and costly.

SUMMARY OF THE INVENTION

The present invention is directed to a rapid exchange catheter extending from a proximal portion which remains outside of a patient's body during use to a distal portion which, during use, is located within a body lumen adjacent to a target area to be treated, wherein the proximal and distal portions are coupled by a medial portion. The catheter comprises a guide wire lumen extending longitudinally through the distal portion and a guide wire receiving channel formed by an outer surface of the medial portion, wherein the guide wire lumen is open to a distal end of the channel.

BRIEF DESCRIPTION OF THE DRAWINGS

The accompanying drawings are included to provide a further understanding of the invention and are incorporated in and constitute part of the specification, illustrate several embodiments of the invention and, together with the description, serve to explain examples of the present invention. In the drawings:

FIG. 1 is a perspective view of a catheter including a rapid exchange channel;

FIG. 2 is a cross-sectional view of the catheter of FIG. 1 taken along line 2-2 thereof;

FIG. 3 is a cross-sectional view of the catheter with guide wire of FIG. 1 taken along line 3-3 thereof;

FIG. 4A is a perspective, partially cross-sectional view of a catheter having a depressible guide wire lumen;

FIG. 4B is a perspective view of the catheter of FIG. 4A with a guide wire inserted through the depressible guide wire lumen;

FIG. 5 is a cross-sectional view of the catheter of FIG. 4A, taken along line 5-5 thereof;

FIG. 6 is a cross-sectional view of the catheter of FIG. 4A, taken along line 6-6 thereof;

FIG. 7 is a perspective view of a catheter according to the present invention received within a working channel of an endoscope;

FIG. 8 is a cross-sectional view of the endoscope and catheter of FIG. 7 taken along line 8-8 thereof;

DETAILED DESCRIPTION

Figure 10:
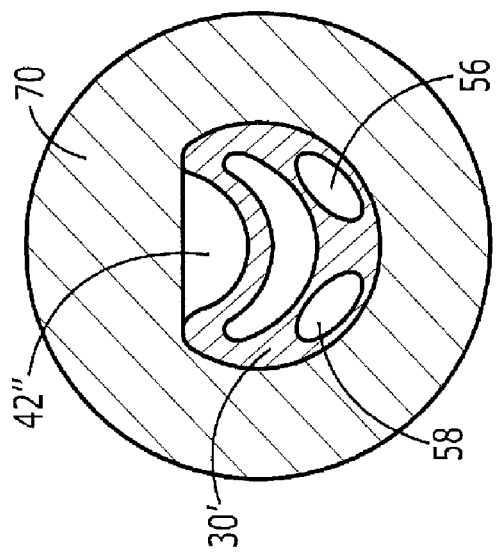
FIG. 10 is a cross-sectional view of the endoscope of FIG. 7 when no guide wire extends through the endoscope.
Figure 9:
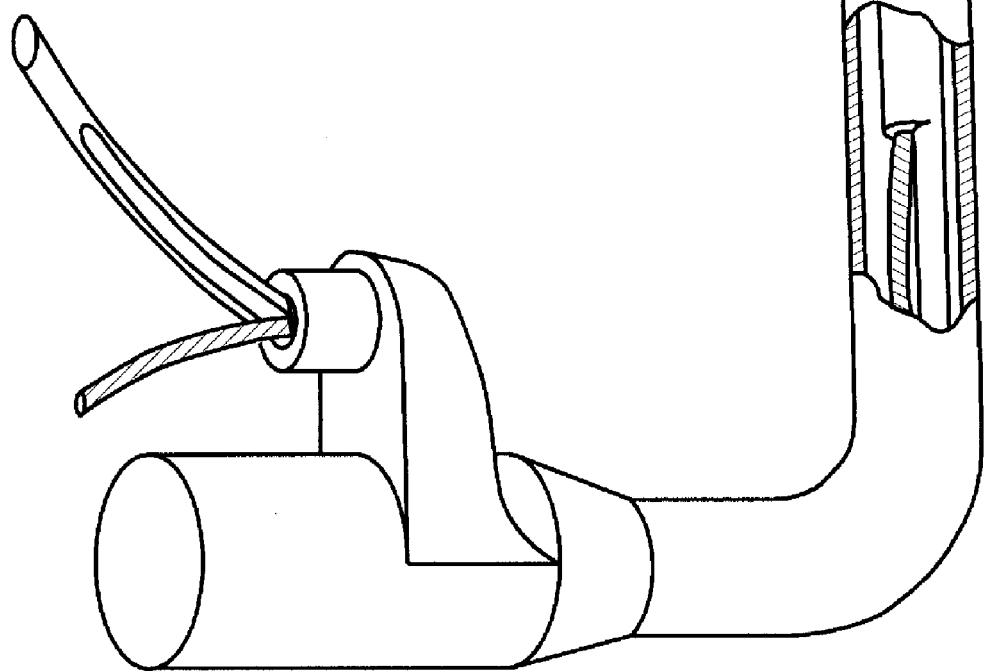
FIG. 9 is a partially cross-sectional view of the endoscope of FIG. 7.

Methods and devices for using catheters to access the biliary tree are disclosed for example in Weaver et. Al., U.S. Pat. No. 5,397,302 and Karpiel, U.S. Pat. No. 5,320,602, the disclosures of which are hereby expressly incorporated by reference herein. Treating an abnormal pathology within a patient's biliary tree may involve introducing an endoscope into the mouth of the patient and guiding the endoscope through the patient's alimentary tract until an opening at a distal end of the endoscope is proximate an area to receive treatment. Those skilled in the art will understand that, although the catheters and methods of use described herein are illustrated in conjunction with procedures for accessing the biliary tree, these catheters may be employed, or modified for employment (e.g., by changing diameter, length, etc.) in procedures to be performed in any body lumen.

For visualization or treatment of a target area within a body lumen, e.g., an area within the biliary tree, the distal end of an endoscope may be positioned proximate the papilla of vater leading to the common bile duct and the pancreatic duct. A catheter may then be guided through the lumen (e.g., a working channel) of the endoscope until a distal tip of the catheter emerges from an opening at the distal end of the endoscope. The catheter may then be advanced through the sphincter into the bile duct. A guide wire may then be advanced through the catheter, as will be described in more detail below, into the bile duct and guided using, e.g., flouroscopy, to a target area to be treated by the catheter. The catheter is then advanced along the guide wire to the target area.

As shown in FIGS. 1-10, one such rapid exchange catheter 30 includes a guide wire lumen 60 including a depressible portion 42 wherein an outer wall of the catheter 30 over the guide wire lumen 60 is collapsed radially inwardly as shown in FIGS. 4A, 4B and 6. As shown in FIG. 4B, partially circumferential slits 52', 54', are formed in an outer wall of the catheter 30 at the depressible portion ends 52, 54 so that openings are formed to the guide wire lumen 60 at the depressible portion ends 52, 54. This allows a guide wire 36 to be inserted into or removed from the guide wire lumen 60 at the depressible portion distal end 54, as described in more detail below. Those skilled in the art will understand that, alternatively, the depressible portion 42 may be formed with an opening only at the distal end 54 as the guide wire 36 enters the guide wire lumen 60 only through the distal end 54. Thus, in a catheter of this type the slit 52' need not be formed at the end 52. Furthermore, those skilled in the art will understand that it would be possible to form an opening to the guide wire lumen 60 at any place in the channel 42'. However, it is preferable to place this opening at the distal end 54 thereof so that the interior space of the catheter is not compromised by both the depressed portion 42 and a guide wire received therein at the same longitudinal position.

As shown in FIGS. 1-10, one such rapid exchange catheter 30 includes a guide wire lumen 60 including a depressible portion 42 wherein an outer wall of the catheter 30 over the guide wire lumen 60 is collapsed radially inwardly as shown in FIGS. 4A, 4B and 6. As shown in FIG. 4A, partially circumferential slits 52', 54', are formed in an outer wall of the catheter 30 at the depressible portion ends 52, 54 so that openings are formed to the guide wire lumen 60 at the depressible portion ends 52, 54. This allows a guide wire 36 to be inserted into or removed from the guide wire lumen 60 at the depressible portion distal end 54, as described in more detail below. Those skilled in the art will understand that, alternatively, the depressible portion 42 may be formed with an opening only at the distal end 54 as the guide wire 36 enters the guide wire lumen 60 only through the distal end 54. Thus, in a catheter of this type the slit 52' need not be formed at the end 52. Furthermore, those skilled in the art will understand that it would be possible to form an opening to the guide wire lumen 60 at any place in the channel 42'. However, it is preferable to place this opening at the distal end 54 thereof so that the interior space of the catheter is not compromised by both the depressed portion 42 and a guide wire received therein at the same longitudinal position.

The fact that the guide wire 36 is received only within a distal portion of the catheter 30 allows the catheter assembly 30 to be exchanged rapidly without the need for guide wire extenders or other devices as described more fully below.

More specifically, FIGS. 1-10 show a catheter 30 including a catheter hub assembly 32 with a guide wire 36 passing through a guidewire lumen 60 which extends through a distal portion thereof. That is, the guide wire 36 extends within the catheter 30 from the depressible portion distal end 54 to a distal end 46 of the catheter 30. The catheter 30 includes a shaft 38 which has a proximal end 40, a depressible portion 42, a distal tip region 44 and various lumens described in greater detail below. The catheter hub assembly 32 is operably connected to a proximal end 40 of the shaft 38. The catheter hub assembly 32 may preferably be configured to couple to ancillary devices allowing access to the lumens within the shaft 38.

In a first embodiment, the shaft 38 may be a generally tubular member having a generally uniform outer shape at the proximal end 40. As would be understood by those of skill in the art, the shaft 38 may preferably be sized for slidable passage through, for example, the working channel of an endoscope 70 or through a body lumen. The shaft 38 may preferably be formed in an extrusion process, and may be formed, for example, of a polymeric material. In one embodiment, the preferred polymeric material is polytetrafluoroethylene, polyether block amide, nylon or a combination or blend of these. Catheters that are contemplated include, but are not limited to, cannulas, sphincterotomes, cytology devices, and devices for stone retrieval and stent placement.

As shown in FIG. 1, the shaft 38 may further include a distal taper 48 that tapers to the distal tip region 44. Additionally, the distal tip region 44 may, for example, include high contrast, color-coded distal markers 50. Finally, the distal end 46 may be radiopaque for fluoroscopic visualization of the distal tip region 44 during a catheter procedure.

In this embodiment, the guide wire lumen 60 extends through the catheter 30 from the proximal end 40 to the distal end 46 thereof. The depressible portion 42 is formed over a portion of the guide wire lumen 60 extending between the depressible portion proximal and distal ends 52, 54, respectively. In this embodiment, the depressible portion 42 is moveable between an expanded configuration in which an outer wall of the lumen 60 is extended radially to form a substantially continuous surface with the rest of the catheter 30 and a depressed configuration in which the outer wall is collapsed into the lumen 60 to form a channel 42' in which a portion of the guide wire 36 may be received. That is, the catheter 30 is preferably formed so that, when in an unstressed state (i.e., with no guide wire 36 passing through the lumen 60), the depressible portion 42 is in the depressed configuration. If a guide wire 36 is inserted into the guide wire lumen 60 from the proximal end 40 to enter that portion of the lumen 60 within the depressible portion 42, the guide wire 36 urges the outer wall of the catheter 30 outward to the expanded configuration.

Those skilled in the art will understand that, if the catheter 30 is not to be used in procedures where guide wire exchanges are contemplated, the guide wire lumen 60 does not need to extend proximally of the depressible portion distal end 54. This would mean that the slit 52' need not be included in such a catheter 30. Furthermore, such a catheter 30 would not need a depressible portion 42 movable between depressed and expanded configurations as no guide wire 36 would ever be received beneath the depressible portion 42 to move it to the expanded configuration. Thus, the depressible portion 42 of such a catheter 30 could be molded permanently in the depressed configuration.

As described above, although the proximal end 52 may be located at any location distal of the proximal end 40 of the shaft 38, it is preferably located at a portion of the catheter 30 which remains proximally outside the endoscope 70 during use. The distal end 54 may be located at any point distal of the depressible portion proximal end 52, but may preferably be located between 10 and 40 cm from the distal end 46 of the catheter shaft 38. The distal opening 54 may more preferably be located between 20 and 30 cm and, most preferably, approximately 25 cm from the distal end 46. As shown in FIGS. 2 and 3, with the exception of the slits 52' and 54', the guide wire lumen 60 of the catheter 30 of FIG. 1 is completely sealed from an outside of the catheter 30.

The catheter 30 according to this exemplary embodiment also includes ancillary lumens 56 and 58 which may be used for a variety of purposes as would be understood by those of skill in the art. As would be understood by those of skill in the art, the ancillary lumens 56 and 58 may preferably extend longitudinally between the proximal end 40 and the distal end 46 of the shaft 38 so that they may be used, for example, as injection lumens, allowing for high contrast media flow capability for bubble-free opacification and for visualization of a desired anatomical region. Additionally or alternatively, the ancillary lumens 56 and 58 may, for example, be used for or serve as part of another ancillary device, such as a cutting wire or a retrieval balloon, etc.

As described above, the catheter 30 of FIG. 1 includes a guide wire lumen 60 that allows rapid exchange of the catheter 30 or the guide wire 36 when an alternative catheter or guide wire is necessary during a medical procedure. Thus, shorter length guide wires may be used since the guide wire 36 does not need to pass through the entire length of the shaft. When the catheter 30 is to be exchanged, an operator grasps the portion of the guide wire 36 extending out of the endoscope 70 and withdraws the catheter 30 proximally therealong while maintaining the position of the guide wire 36 at the target location. As only a short portion of the guide wire 36 is received within the catheter 30, the user may maintain his grasp on the guide wire 36 until the distal end 46 of the catheter exits the proximal end of the endoscope 70. At this time, the user may grasp the portion of the guide wire 36 extending distally from the distal end 46 and completely remove the catheter 30 from the guide wire 36 without ever letting go of the guide wire 36 and without resorting to guide wire extenders, etc.

Of course, if desired, the guide wire 36 may also run through the entire length of the lumen 60 from the proximal end 40 of the catheter 30 to the distal end 46 thereof, for example, if the catheter 30 is maintained in place while the guide wire 36 is removed therefrom. A new guide wire 36 may then be inserted through the entire length of the catheter 30 moving the depressible portion 42 from the collapsed to the expanded configuration. However, after this has been done, the effectiveness of the rapid exchange features of this catheter 30 may be reduced.

As shown in FIG. 4, the channel 42' merges with the guide wire lumen 60 at both ends thereof and may be used as an entry point for the guide wire 36. Those skilled in the art will understand that only the depressible portion distal end 54 needs to be open to the guide wire lumen 60 as the guide wire 36 will preferably extend from the guide wire lumen 60 through the slit 54' (which, when the catheter 30 is in the depressed configuration, forms an opening) into the channel 42'. As described above, the catheter 30 may be formed so that the depressible portion 42 remains in the depressed configuration unless a guide wire 36 is received within the depressible portion 42 of the lumen 36 pushing the outer wall of the catheter 30 outward. Those skilled in the art will understand that the channel 42' may be formed by mechanically deforming or crushing the shaft 38 and may be induced to remain in this position by, for example, heating the designated area of the shaft 38 where the channel 42' is sought. The heat may make the polymeric material of which the shaft 38 is composed more malleable allowing the catheter 30 to retain the shape including channel 42'.

In addition, as described above, partially circumferential slits 52', 54', may be cut at the ends of the channel 42' substantially perpendicular to the longitudinal axis of the catheter 30 to allow the proximal and distal ends of the depressible portion 42 to separate from adjacent portions of the catheter 30 when the catheter is moved to the depressed configuration. FIG. 5 shows a cross-sectional view of the depressible portion 42 of the shaft 38 in the expanded configuration while FIG. 6 shows the catheter 30 in the depressed configuration. Alternatively, as shown in FIG. 10, a catheter 30' may be formed with a channel 42'' which is permanently in the collapsed configuration.

As would be understood by those of skill in the art, the viscosity of bodily fluids, such as bile, allows them to travel through the working channel of the endoscope, along the outer walls of catheters under capillary action causing risk of contamination if these fluids escape. To guard against this, a rubber seal is often placed around the catheter 30 within the working channel. As would be understood by those of skill in the art, in contrast with catheters having discontinuities in their outer skins due to channels opening therethrough, the smooth surface of the outer wall of the catheter 30 in the depressed portion 42 with only rounded surfaces allows for a better seal to be obtained therearound.

Another advantage of the depressible portion 42 is that it increases the columnar strength of the shaft 38 as compared to catheters which have longitudinally extending channels cut through their outer surfaces. As the channel 42' of the catheter 30 is formed without removing any material from the outer surface thereof, the column strength of the catheter 30 is maintained substantially equivalent to that of standard catheters with no rapid exchange features. As shown in FIG. 6, the shaft 38 contains ancillary lumens 56 and 58, and the depressed lumen 61.

As described above, the channel 42' may be used as an entry point for a guide wire 36, as the guide wire 36 may be inserted into the guide wire lumen 60 via the distal opening 54. As also described above, the channel 42' allows for rapid exchange of the catheter 30 when an alternative catheter is necessary during a medical procedure. Shorter length guide wires may be used since guide wire 36 does not pass through the shaft proximal end 40 and hub assembly 32, but rather exits the shaft 38 at a location at least as removed distally from the proximal end 40 as the distal opening 54.

The present invention may be incorporated into most existing conventional catheter procedures since, with the exception of guide wire exchange, the catheter according to this invention is not substantially different in operation from these known catheters.

In one possible endoscopic procedure, an endoscope is first introduced into a patient's mouth and is guided down the esophagus, through the stomach, past the pyloric sphincter of the stomach and into the duodenum. The endoscope is then guided through the alimentary canal until a distal end of the endoscope is proximate to a target area that requires treatment. For instance, in an endoscopic biliary procedure, the endoscope is guided into the duodenum until the opening at the distal end of the endoscope is proximate the papilla of vater.

Once the endoscope has been properly positioned within the patient, the catheter 30 is inserted into the endoscope and advanced therethrough to exit at the distal end of the endoscope. A guide wire 36 is then inserted into the guide wire lumen 60 of a catheter 30 and the catheter 30 and the guide wire 36 are then advanced through the sphincter into the bile duct. The guide wire 36 is then advanced through the guide wire lumen 60 to exit the distal end 46 of the catheter 30 and enter the bile duct. As would be understood by those of skill in the art, the guide wire 36 may then be advanced through the bile duct to the target area and the shaft 38 may then be advanced over the guide wire 36 to the target area.

As would be understood by those of skill in the art, once the guide wire 36 has been positioned at the target area, various catheter procedures may be performed. For example, contrast media, such as radiopaque dye, may be injected thereto via the ancillary lumens 56 or 58 to allow visualization of the area. After the desired catheter procedure has been completed, the catheter 30 may need to be exchanged.

At this point, the physician simply draws the catheter 30 proximally along the guide wire 36 while grasping the proximal end of the guide wire 36. When the distal end of the catheter 30 exits the body, the physician may grasp the portion of the guide wire 36 extending distally of the catheter 30 and remove the catheter 30 completely from the guide wire 36. The loading process described above may then be repeated for the new catheter 30 to be used. If, however, the physician wishes to exchange the guide wire 36 while maintaining the catheter 30 in a desired position within the body, the following steps are performed. First, while grasping the proximal end of the catheter 30, the physician draws the guide wire 36 proximally out of the guide wire lumen 60 and removes it from the body. Then, the new guide wire 36 is inserted into the proximal opening 52 and is fed through the guide wire lumen 60 through the C-channel 42 so that it deflects the outer wall of the depressible portion 42 radially outward to allow the guide wire 36 to pass thereunder, past the distal opening 54 and out of the distal end 46 of the catheter 30.

If a guide wire 36 has been inserted from the proximal end 40 of the catheter 30, past the proximal opening 52, through the depressible portion 42 to the distal end 46 thereof and this catheter 30 later needs to be exchanged while maintaining the guide wire 36 in position, the physician grasps the proximal end of the guide wire 36 to maintain it in position and grasps the guide wire 36 through the proximal opening 52 and draws the proximal end of the guide wire 36 distally through the proximal portion of the guide wire lumen 60 while holding the distal portion of the guide wire 36 stationary to maintain the position of the distal end of the guide wire 36. When the proximal end of the guide wire 36 has been removed from the guide wire lumen 60, the catheter 30 may be drawn proximally from the body while the physician maintains his grasp of the guide wire 36 as it slides out of the proximal opening 52. When the distal end of the catheter 30 is outside the body, the physician grasps the portion of the guide wire 36 extending distally of the distal end of the catheter 30 and withdraws the catheter 30 from the guide wire 36.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

The invention claimed is:

1. A rapid exchange catheter comprising:
 a guide wire lumen; and
 first and second slits separated from one another longitudinally along a portion of the catheter forming a depressible portion of a wall of the catheter therebetween, the depressible portion being movable between a depressed configuration in which an inner surface of the depressible portion is moved a predetermined distance radially inward toward an inner surface of an opposite side of the guide wire lumen to form a guide wire receiving channel and a non-depressed configuration, the predetermined distance being selected so that, when a guide wire is received in the guide wire receiving channel, a combined diameter of the guide wire and the catheter is no greater than a diameter of the catheter in the non-depressed configuration;
 wherein the depressible portion has a continuous wall surface having a substantially uniform wall thickness when in the non-depressed configuration.

2. The catheter according to claim 1, wherein, when in the depressed configuration, at least one of the first and second slits forms an opening to the guide wire lumen.

3. The catheter according to claim 1, wherein the first and second slits are transverse, partially circumferential cuts in the catheter wall.

4. The catheter according to claim 1, wherein the depressible portion is biased to the depressed configuration.

5. The catheter according to claim 1, wherein the first slit is distal to the second slit, and the first slit is between about 10 cm and 40 cm from a distal end of the catheter.

6. The catheter according to claim 1, wherein the first slit is between about 20 cm and 30 cm from the distal end of the catheter.

7. The catheter according to claim 1, wherein the first slit is about 25 cm from the distal end of the catheter.

8. The catheter according to claim 1, wherein the guide wire lumen extends distally only through a portion of the catheter distal to the first slit.

9. A rapid exchange catheter comprising:
 a guide wire lumen;
 a depressible portion of a wall of the catheter biased toward a depressed configuration in which the depressible portion is moved radially inward a predetermined distance to form a guide wire receiving channel, a first opening from a first end of the guide wire receiving channel to the guide wire lumen is formed so that, in a non-depressed configuration, an outer surface of the first end of the guide wire receiving channel forms a substantially continuous outer surface with an outer surface of an adjacent portion of the catheter wall.

10. The catheter according to claim 9, wherein the guide wire receiving channel includes a second opening from a second end of the guide wire receiving channel to the guide wire lumen.

11. The catheter according to claim 9, wherein the guide wire lumen extends only through a distal portion of the catheter.

12. The catheter according to claim 9, wherein the first end of the guide wire receiving channel is between about 10 cm and 40 cm from a distal end of the catheter.

13. The catheter according to claim 9, wherein the first end of the guide wire receiving channel is between about 20 cm and 30 cm from the distal end of the catheter.

14. The catheter according to claim 9, wherein the first end of the guide wire receiving channel is about 25 cm from the distal end of the catheter.

15. The catheter according to claim 9, wherein the predetermined distance is selected so that, when a guide wire is received in the guide wire receiving channel, a combined diameter of the guide wire and the catheter is no greater than a diameter of the catheter in the non-depressed configuration.

16. A method for treating tissue, comprising:
 configuring a depressible portion of a wall of a catheter in a depressed configuration to form a guide wire receiving channel with an opening from the guide wire receiving channel to a guide wire lumen, the catheter having a non-depressed configuration in which the depressible portion of the wall of the catheter is moved radially outward a predetermined distance relative to the depressed configuration;
 inserting a guide wire into the guide wire receiving channel so that a combined diameter of the guide wire and the catheter is no greater than a diameter of the catheter in the non-depressed configuration;
 inserting the guide wire through the opening of the guide wire receiving channel into the guide wire lumen; and
 advancing the guide wire through the body lumen to a desired location therein.

17. The method according to claim 16, further comprising:
 grasping a first portion of the guide wire proximal of the opening;

withdrawing the catheter proximally over the guide wire until the distal end of the catheter is within a predetermined distance of the first portion;
grasping a second portion of the guide wire distal of the distal end of the catheter; and
removing the catheter from the guide wire.

18. The catheter according to claim 1, further including one or more ancillary lumens.

19. The catheter according to claim 9, further including one or more ancillary lumens.

\* \* \* \* \*

UNITED STATES PATENT AND TRADEMARK OFFICE
CERTIFICATE OF CORRECTION

PATENT NO. : 8,298,178 B2
APPLICATION NO. : 12/254425
DATED : October 30, 2012
INVENTOR(S) : Oscar Carrillo, James E. Windheuser and M. Kevin Richardson Page 1 of 1

It is certified that error appears in the above-identified patent and that said Letters Patent is hereby corrected as shown below:

Column 3
Lines 20-42, delete paragraph and insert therefor

-- The guide wire 36 may be received within a channel 42' formed by the depressible portion 42 so that, even though the guide wire 36 extends outside the catheter 30 along the depressible portion 42, an outer diameter of this assembly is no greater than an outer diameter of the catheter 30 alone. As shown in FIG. 7, the catheter 30 and the guide wire 36 may fit comfortably within the working channel of an endoscope 70. Thus, the depressible portion proximal end 52 is preferably located on a portion of the catheter 30 which will remain proximally outside the endoscope 70 during use. --.

Signed and Sealed this
Fifteenth Day of January, 2013

David J. Kappos
*Director of the United States Patent and Trademark Office*